United States Patent [19]

Phillips, Jr. et al.

[11] Patent Number: 4,919,135
[45] Date of Patent: Apr. 24, 1990

[54] TRIAXIAL ELECTRODE

[75] Inventors: Richard E. Phillips, Jr., San Marcos; Paul R. Spehr, Lake Jackson, both of Tex.

[73] Assignee: Intermedics, Inc., Angleton, Tex.

[21] Appl. No.: 284,106

[22] Filed: Dec. 14, 1988

[51] Int. Cl.[5] ............................................. A61N 1/00
[52] U.S. Cl. .................................. 128/419 P; 128/786
[58] Field of Search ........ 128/419 P, 419 G, 784–786, 128/642

[56] References Cited

U.S. PATENT DOCUMENTS

| | | | |
|---|---|---|---|
| 4,570,642 | 2/1986 | Kane et al. | 128/419 P |
| 4,649,938 | 3/1987 | McArthur | 128/419 P |
| 4,667,686 | 5/1987 | Peers-Travarton | 128/419 P |
| 4,679,572 | 7/1987 | Baker, Jr. | 128/419 P |

Primary Examiner—Francis Jaworski
Assistant Examiner—George Manuel
Attorney, Agent, or Firm—John R. Merkling

[57] ABSTRACT

A lead assembly for a cardiac pacemaker is formed by an electrical conductor having one end connected to the pacemaker and a heart engaging electrode member attached to the opposite end. The electrode member has a profiled contact surface having at least one diametrically extending groove and a coating of iridium oxide thereon. The profiled electrode member offers at least a pair of edges to both grip the heart tissue to reduce relative movement of the electrode while focusing the discharge of the pulses thereby allowing reduction in the polarizing pacing voltage.

24 Claims, 3 Drawing Sheets

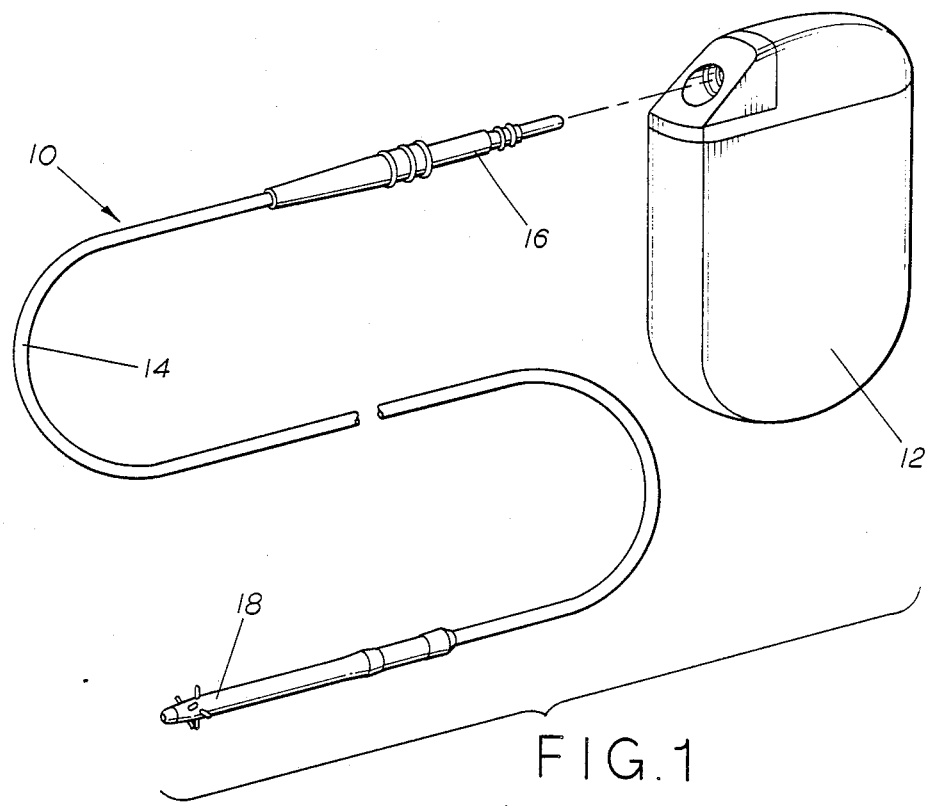
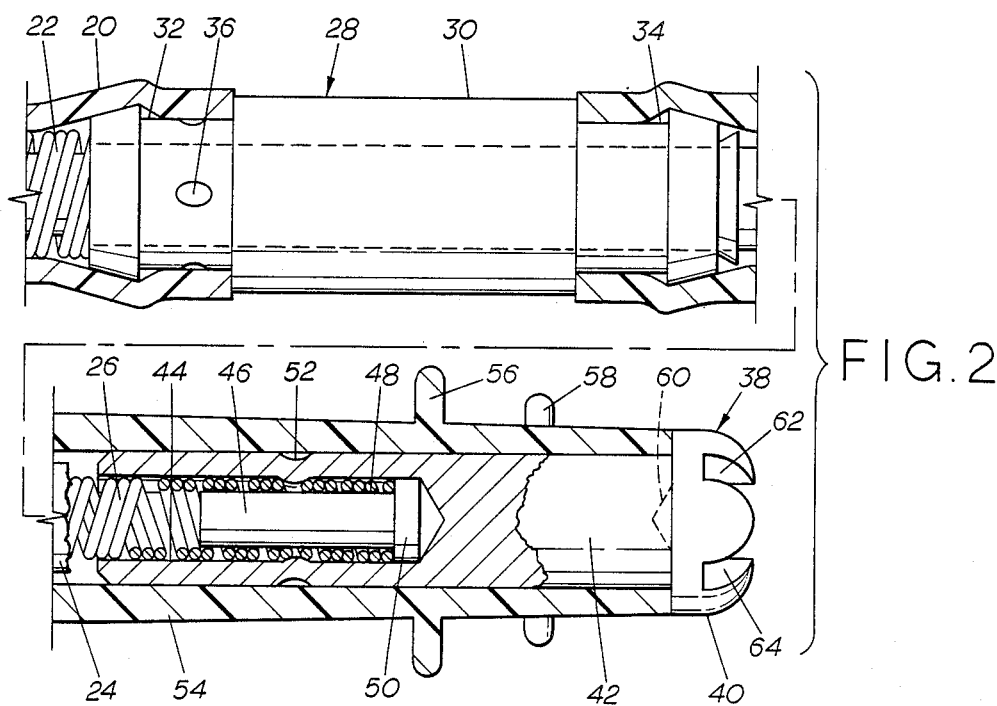

TRIAXIAL ELECTRODE

BACKGROUND OF INVENTION

1. The Field of the Invention

The present invention relates generally to cardiac pacing and more particularly to an improved electrode for use in stimulating or sensing electrical activity of the heart and to pacing lead assemblies incorporating such electrodes.

2. The Prior Art

It is well known that the sinoatrial (SA) node of the normal mammalian heart acts as the natural pacemaker by which rhythmic electrical excitation is developed and propagated in the atria. In response the atrial chambers contract pumping blood to the ventricles. The excitation is propagated in the atrioventricular (AV) node, which imposes a delay, and then via the conduction system consisting of the bundle of His and Purkinge fibers to the ventricle muscle causing contraction and pumping of blood from the ventricles. Disruption of the natural pacing/propagation system occurs as a result of aging and disease.

Where normal rate or rhythm is not spontaneously maintaining the heartbeat of a human patient, the condition is corrected typically by utilization of an implantable cardiac pacemaker selected according to the particular deficiency of the patient. In its simplest form, the cardiac pacemaker consists of a pulse generator powered by a self contained battery pack; a lead assembly including an electrode adapted to be positioned in stimulating relationship to excitable myocardial tissue either externally (an epicardial electrode) or internally (an endocardial electrode) of the heart, and an insulated electrically conductive lead interconnecting the pulse generator to the tissue to deliver electrical stimuli to the tissue; and a second electrode connected to a reference potential, by which the electrical circuit is completed via body tissue and fluids. The entire lead assembly is often referred to simply as the lead and the terminology "lead" and "electrode" are sometimes used interchangeably, albeit inaccurately.

The customary lead choice for the implantable cardiac pacemaker is an endocardial lead or leads because it is readily inserted perveniously to introduce the stimulating electrode directly into the chamber of the heart which is to be paced. In contrast, an epicardial lead requires thoracic surgery to affix the electrode to the heart's outer surface. In either case various means are employed to insure maintenance of positioning of the electrode relative to the excitable heart tissue. For epicardial leads, active fixation, such as sutures or a sutureless screw-in electrode, is employed. Endocardial leads may utilize active fixation, such as a corkscrew, or passive fixation, which is less invasive, in the form of flexible barbs or hooks.

In operation, the output pulses from the pulse generator of a cardiac pacemaker are delivered via the lead for electrical stimulation of the excitable myocardial cardiac tissue at or in the immediately vicinity of the site of the cathode to produce the desired rhythmic contraction of the affected chamber. As is well known, stimulation is attributable to current density and hence small area electrodes will suffice inasmuch as the current required to produce a given current density decreases in direct proportion to the active area of the electrode. Small area electrodes (cathodes) therefore serve to prolong battery life resulting in a lengthening of the interval between required pacemaker replacements.

In essence, stimulation requires that an electrical field of sufficient strength and current density be impressed upon the excitable tissue in the vicinity of the cathode site to initiate contraction. The minimum electrical impulse necessary to produce that effect is referred to as the stimulation threshold. The greater the efficiency of the cathode in impressing the electric field on the tissue, the smaller is the amplitude and/or duration of the pulse required to exceed the threshold. Accordingly, high efficiency low threshold electrodes conserve energy and prolong battery life. Some authorities have theorized that because greater electrical efficiency lowers the electrical energy required for stimulation, it is a factor in reducing injury to the tissue at the stimulation site.

The chronic stimulation threshold for a given patient is typically on the order of two to three times greater than the acute threshold observed at the time of implantation and within the first few days thereafter. The increase in threshold is attributed to fibrotic growth; that is the formation of a layer of non-excitable tissue about the electrode tip at the stimulation site. This fibrotic layer creates a virtual electrode surface area which is consistently greater than the actual surface area of the electrode and consequently raises the stimulation threshold. Interestingly, the increase of chronic threshold over acute threshold is proportionately greater (to a limit) as the electrode area is decreased, presumably because the ratio of virtual to actual surface is higher for small area electrodes. Many authorities have speculated that the particular composition of the electrode may contribute to or retard fibrotic growth.

It becomes quite clear from the prior art studies that there are two factors which have a significant impact on the efficiency of the electrode tip. These factors are the shape of the electrode and the composition of matter forming the electrode. The shape of the electrode, as discussed above, should be kept to a minimum size while the surface area should be maximized as the greater amount of contact area allows a direct reduction in the electrical energy usage. The composition of matter making the electrode tip or coating/plating on the tip also will directly effect the efficiency of the transfer of electrical energy to the tissue as well as may have an effect on deterring the fibrotic growth.

There are two patents which are particularly representative of the prior art, namely U.S. Pat. Nos. 4,649,937 to DeHaan et al. and 4,679,572 to Baker. The former patent teaches an electrode tip member which has a rounded or bullet shaped distal end with grooves etched into the end to increase the surface area of the electrode member within the small displaced surface area to minimize polarization of the tip member while insuring sufficient electrical current flow to cause heart muscle depolarization. Preferably the tip electrode member is made of titanium or titanium alloy and is coated with carbon. The Baker patent teaches an electrode for use in cardiac pacemaking having a conductive tip portion including a substrate composed of material conventionally employed for pacing electrodes and a layer or film of iridium oxide overlying the surface of the substrate. The tip portion may be provided with recesses which confine the iridium oxide surface and an iridium oxide layer may be formed on both the cathode and anode portions of a bipolar lead for efficient transduction of the electrode electrolyte interface in the environment of the cardiac pacemaker patient's body.

SUMMARY OF THE INVENTION

The present invention constitutes an improvement over the electrodes of the prior art in that it provides a specific profiled arrangement of the electrode tip with the tip further being coated with a material to reduce the voltage threshold while enhancing the contact area. The preferred arrangement is to have one to three substantially diagonally extending grooves formed in the end of the electrode tip which will engage the tissue. This configuration allows a degree of penetration of the tip into the tissue thereby enhancing the contact there between.

BRIEF DESCRIPTION OF THE DRAWINGS

The present invention will now be described by way of example with reference to the accompanying drawings in which:

FIG. 1 is a perspective view of a cardiac pacemaker with a lead according to the present invention exploded therefrom;

FIG. 2 is an enlarged detailed view, partly in section, of the electrode end of the lead of FIG. 1;

DETAILED DESCRIPTION OF THE PREFERRED EMBODIMENTS

Figure 3:
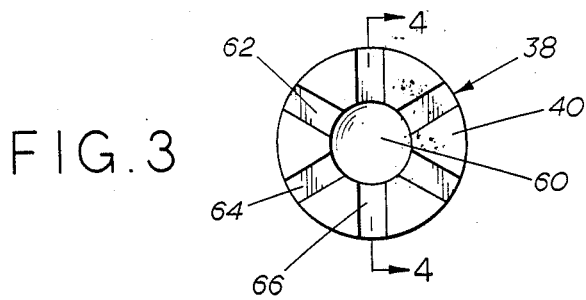
FIG. 3 is an end view of the tip of the electrode shown in FIG. 2.

A typical cardiac pacemaker assembly 10 is shown in FIG. 1 and comprises an implantable cardiac pacemaker 12 and at least one lead assembly 14 which is connected thereto. The cardiac pacemaker 12 generally includes circuitry for sensing electrical activity of the heart and for generating pacing signals as required by the heart. The lead assembly 14, which may be either unipolar or bipolar, includes a proximal connector portion 16 that plugs into a mating connector receptacle of the pacemaker and a distal head portion 18 that may be passed along a vein to lodge within the interior of the heart. The lead assembly 14 contains electrical conducting wires which connect the proximal connector 16 to the distal head portion 18 so that electrical signals can be transmitted from the pacemaker to stimulate the heart at the tip of the distal head portion. The conductors also allow electrical signals occurring in the heart to be transmitted from the distal head portion to the pacemaker for detection by circuitry within the pacemaker.

FIG. 2 illustrates the distal head portion 18 in side elevation, partially in section. The illustrated lead 14 has a bipolar configuration and includes an outer sheath 20, an outer electrically conducting coil 22, an inner sheath 24, and an inner electrically conducting coil 26. Both sheaths 20 and 24 are preferably made of any suitable biocompatible insulating material, for example polyurethane or silicone rubber. The outer and inner electrically conducting coils 22 and 26 are coaxial and preferably formed from helically wound nickel cobalt alloy wire or similar material 4 - 9 mils thick. A tubular anode electrode 28 is formed of conductive material with a central portion 30 of a first outer diameter and profiled end portions 32 and 3 of lesser outer diameters adapted to be received within outer sheath 20. The anode electrode 28 is secured mechanically and electrically to outer coil 22 by crimps 36. The distal end of the head 18 includes an electrically conducting tip cathode electrode 38 having a profiled head portion 40, a shaft body portion 42, and a first counter-bore 44. The inner conducting coil 26 is received in the counter-bore 44 and in turn receives therein a head member 46 formed by a shaft 48 of a diameter sufficiently small to be received in the spring coil 26 and an integral enlarged head portion 50. This head member provides support for the inner assembly of inner coil 26 and tip 38 is received in one end of insulative sheath 54 which has a plurality of resilient tines 56, 58 which, in this case, are shown extending outwardly substantially radially from the lead assembly. Tines of different shapes or other fixation means could be substituted for the illustrated tines without departing from the spirit or essential characteristics of the present invention. One end of the sheath 54 receives therein the end 34 of anode electrode 28.

Figure 4:
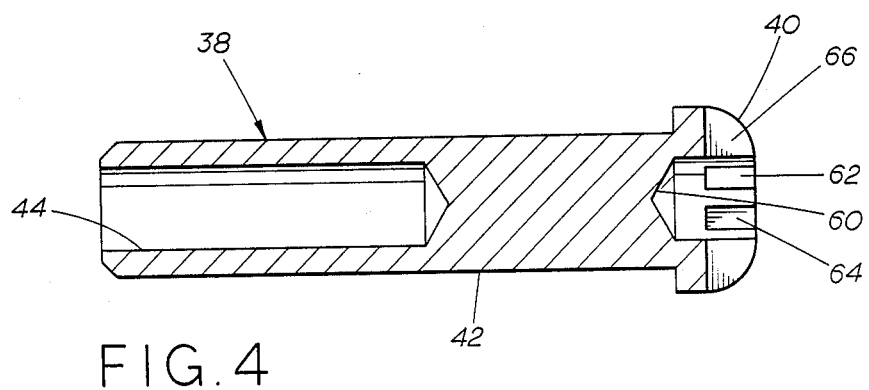
FIG. 4 is a longitudinal section through the electrode portion only of the lead of FIG. 2.

The head portion 40 of the electrode 38 is shown with an axial second counter-bore 60 and three intersecting diametric grooves 62, 64, and 66, as best shown in FIGS. 3 and 4.

Figure 5:
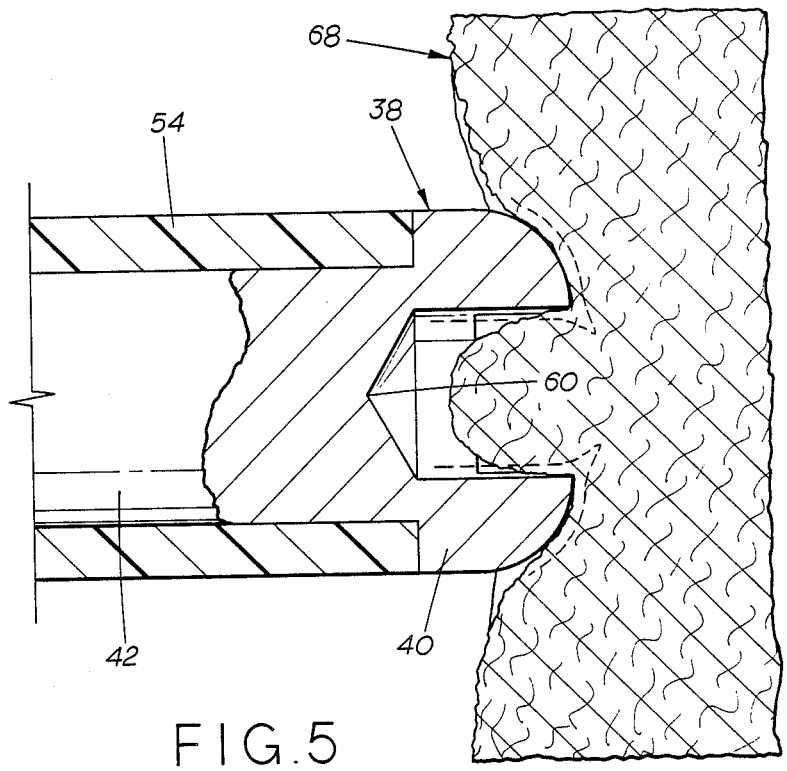
FIG. 5 is an enlarged section detailing the engagement of the subject electrode tip with tissue.

Turning now to FIG. 5, it will be seen how the present invention is utilized. By pressing the tip of the electrode 38 into the heart tissue 68, the tissue will shift to receive portions of the tip while penetrating the open grooves formed in the electrode. Thus the electrode will have maximum surface contact with the tissue.

Figure 6:
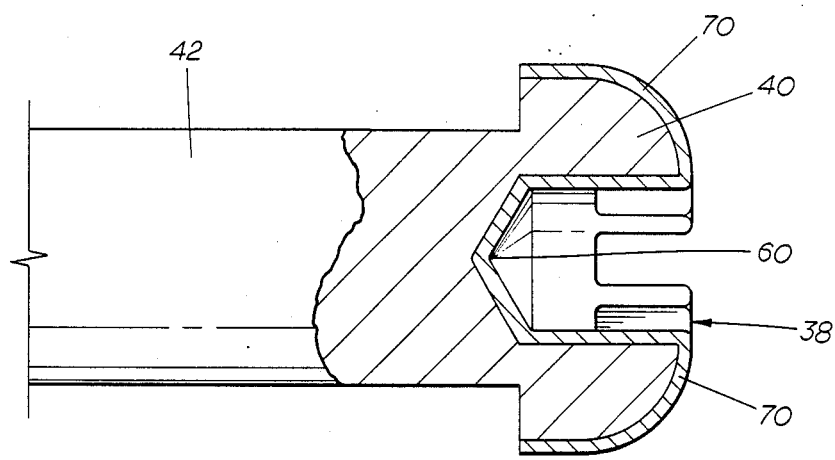
FIG. 6 is an enlarged detail of the subject electrode, partly in section, similar to FIG. 4 with an iridium oxide coating shown in exaggerated thickness.
Figure 7:
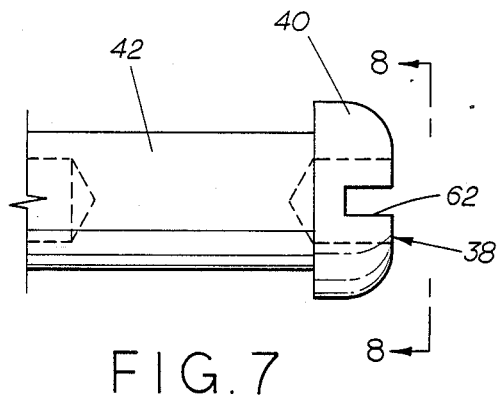
FIG. 7 is a side elevation of the subject electrode showing an alternate embodiment of the present invention.
Figure 8:
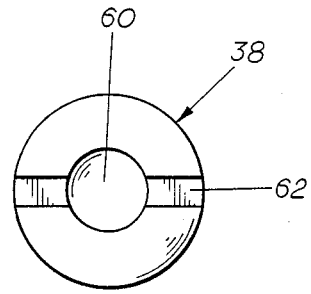
FIG. 8 is a end view of the electrode tip of FIG. 7.
Figure 9:
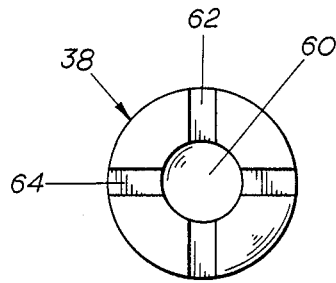
FIG. 9 is a end view of a further alternate embodiment of the subject electrode tip.
Figure 10:
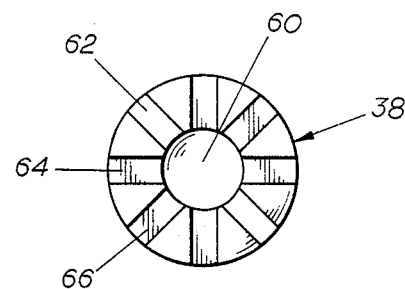

FIGS. 3, 4, and 6 - 10 show the details of the head portion 40 which is generally an enlarged smooth surface of transition intersected by at least one groove 62 extending across a diameter thereof and an axial second counter-bore 60. The preferred number of grooves is from one to three as shown in FIGS. 8, 9, and 3, respectively, which together with the axial second counter-bore will form two to six separate grooves. As shown in FIGS. 4, 6 and 7, the grooves have a bottom or nadir which is linear along the length of the groove. In the preferred embodiment, the bottoms of the grooves are planer and are perpendicular to a longitudinal axis of the lead assembly. This configuration has the particular advantage of being able to make an intimate gripping contact with the heart tissue without requiring a screw for penetration of the heart tissue, as is the case for the above-mentioned U.S. Pat. No. 4,679,572. This configuration is also far simpler to form on the small diameter component of the present invention than is possible with the complex configurations shown by DeHaan et al.

Referring specifically to FIG. 6, the electrode 38 of the present invention is coated with a film or layer 70 of iridium oxide. The preferable method for coating the substrate is by chemical deposition with chloroiridic acid (hydrogen hexochoroiridate IV hydrate) and thermal oxidation of the coating at 300°–500° C. for 2–10 hours. This gives a thickness of 1–500 nanometers of iridium oxide. This type of coating method for thermally depositing iridium oxide is more fully explained in U.S. Pat. Nos. 4,677,989 and 4,717,581, the disclosures of which are incorporated herein by reference. The surface layer preferably has a thickness on the order of 200 nanometers, although layer thickness exceeding about 100 nanometers appears to be satisfactory to obtain the desired result. Preferably the electrode substrate is of a solid structure with a roughened surface to hold the IROX coating thereon, although the invention is not so limited. A porous substrate would allow the iridium oxide coating will follow the lattice-work contour and a porous surface is useful in promoting cardiac tissue ingrowth and thereby reduce abrasion.

The substrate may be reactively coated with iridium oxide in a conventional diode RF sputtering system. First, the substrate is positioned and maintained in good thermal contact with a water cooled platform of the sputtering system. Any portion of the surface which is not to be coated is suitably masked. Pre-sputtering is performed with an iridium target in pure oxygen at an ambient pressure of about 20 microns for approximately 20 minutes to one half hour. The pressure is then reduced to the range of from about 2–4 microns and sputtering is performed with a target power density of about 0.6 to 0.8 watts per square centimeter. The process is continued until the iridium oxide layer of the desired thickness is deposited, about three hours for a 200 nanometer thickness.

The efficient transduction of the iridium oxide layer on the cathode tip results in a low threshold stimulation of excitable heart tissue in the vicinity of the stimulation site under the influence of the electric field. Acute stimulation thresholds as low as approximately 0.2 volts have been observed in canine tests using a ring tip simulating cathode of the type described with reference to FIG. 2.

The grooves in the tip of the present invention increase the surface contact area thereby reducing the polarizing pacing voltage. The grooves also improve stability of the tip by reducing its capability for movement. The grooves further improve pacing threshold by offering edges to discharge the pulses thereby focusing the charge.

Other embodiments of the present invention will be apparent to those skilled in the art to which the invention pertains from a reading of the foregoing description in conjunction with the accompanying drawings. Accordingly, the invention is to be limited only as defined by the appended claims.

We claim

1. A cardiac pacing lead assembly comprising:
   electrode means defining a longitudinal axis and a tip portion provided with an exposed surface having at least one groove extending perpendicular to said longitudinal axis therein, said groove having a linear nadir portion, said tip portion being electrically adapted to be coupled with excitable cardiac tissue of a heart when said lead assembly is implanted in a patient for stimulating the cardiac tissue when said electrode means is electrically energized; and
   electrical conductor means electrically connected at one end thereof to said electrode means for delivering electrical energy thereto, said conductor means having terminal means at the other end for connection to a pulse generator of a cardiac pacemaker.

2. A cardiac pacing lead assembly according to claim 1 wherein the linear nadir portion of said at least one groove is perpendicular to a longitudinal axis of the lead assembly.

3. A cardiac lead assembly according to claim 2 wherein the linear nadir portion of said at least one groove comprises a planer base.

4. A cardiac pacing lead assembly according to claim 3 further comprising:
   an axial bore extending inwardly from said exposed surface of said tip portion, the axial bore having a diameter greater than the maximum width of said at least one groove.

5. A cardiac pacing lead assembly according to claim 1 further comprising:
   a plurality of diametrically extending grooves, said grooves intersecting said longitudinal axis of the lead assembly, and adjacent grooves forming similar angles.

6. A cardiac pacing lead assembly according to claim 5 further comprising:
   three diametrically extending grooves, each groove having a linear nadir portion.

7. A cardiac lead assembly according to claim 6 wherein the linear nadir portion of each of said grooves comprises a planar base.

8. A cardiac pacing lead assembly according to claim 7 further comprising:
   an axial bore extending inwardly from said exposed surface of said tip portion, the axial bore having a diameter greater than the maximum width of the grooves.

9. A cardiac pacing lead assembly according to claim 5 further comprising:
   ring electrode means spaced away from said electrode means;
   second electrical conductor means electrically connected at one end thereof to said ring electrode means, said second electrical conductor means having terminal means at the other end for connection to the pulse generator of the cardiac pacemaker.

10. A cardiac pacing lead assembly according to claim 5 wherein the exposed surface further comprises a layer of iridium oxide.

11. An implantable cardiac pacemaker for stimulating electrical activity of a heart comprising:
    pulse generator means;
    means for supplying electrical power to said pulse generator means;
    electrode means defining a longitudinal axis and a tip portion with an exposed surface including at least one groove extending perpendicular to said longitudinal axis, said groove having a linear nadir portion, said electrode means adapted for electrically stimulating excitable cardiac tissue of a heart when electrically energized; and
    conductor means having a distal end and a proximal end, said distal end electrically connected to said electrode means and said proximal end electrically connected to said pulse generator means.

12. The implantable cardiac pacemaker according to claim 17 wherein said tip portion of said electrode means has at least three intersecting diametric grooves.

13. An implantable cardiac pacemaker according to claim 11 wherein said tip portion of said electrode means is coated with a film of iridium oxide.

14. The implantable cardiac pacemaker according to claim 7 wherein said at least one groove is perpendicular to a longitudinal axis of the electrode means.

15. The implantable cardiac pacemaker according to claim 14 wherein the linear nadir portion of said at least one groove comprises a planer base.

16. The implantable cardiac pacemaker according to claim 15 further comprising:
   an axial bore extending inwardly from said exposed surface of said tip portion, the axial bore having a diameter greater than the maximum width of said at least one groove.

17. The implantable cardiac pacemaker according to claim 11 further comprising:
   A plurality of diametrically extending grooves, said grooves intersecting near said longitudinal axis of the lead assembly, and adjacent grooves forming similar angles.

18. An improved implantable electrode for use in combination with a cardiac pacemaker, said electrode comprising a generally cylindrical member of electrically conductive material having a proximal end and generally blunted hemispherically shaped distal end, and at least one diametrically extending groove spanning the said distal end, said groove having a linear nadir portion.

19. The implantable electrode according to claim 18 wherein the linear nadir portion of said at least one groove is perpendicular to a longitudinal axis of the electrode.

20. The implantable electrode according to claim 19 wherein the linear nadir portion of said at least one groove comprises a planer base.

21. The implantable electrode according to claim 10 further comprising:
   an axial bore extending inwardly from said distal end, the axial bore having a diameter greater than the maximum width of the at least one groove.

22. The implantable electrode according to claim 18 further comprising:
   a plurality of diametrically extending grooves, said grooves intersecting near a longitudinal axis of the electrode, and adjacent grooves forming similar angles.

23. The implantable electrode according to claim 22 further comprising:
   An array of at least three grooves in said distal end, said array being symmetric around the longitudinal axis of the electrode.

24. A cardiac pacing lead assembly according to claim 23 wherein the exposed surface further comprises a layer of iridium oxide.

* * * * *